(12) United States Patent
Wang et al.

(10) Patent No.: US 7,907,772 B2
(45) Date of Patent: Mar. 15, 2011

(54) DELINEATION ON THREE-DIMENSIONAL MEDICAL IMAGE

(75) Inventors: Bai Wang, Palo Alto, CA (US); Hongwu Wang, Milpitas, CA (US)

(73) Assignee: Accuray Incorporated, Sunnyvale, CA (US)

( * ) Notice: Subject to any disclaimer, the term of this patent is extended or adjusted under 35 U.S.C. 154(b) by 948 days.

(21) Appl. No.: 11/395,666

(22) Filed: Mar. 30, 2006

(65) Prior Publication Data

US 2007/0230765 A1 Oct. 4, 2007

(51) Int. Cl.
*G06K 9/00* (2006.01)
(52) U.S. Cl. .................................... 382/154; 382/128
(58) Field of Classification Search .................. 382/154
See application file for complete search history.

(56) References Cited

U.S. PATENT DOCUMENTS

| | | | | |
|---|---|---|---|---|
| 5,568,384 A * | 10/1996 | Robb et al. | ...................... | 715/202 |
| 6,514,082 B2 * | 2/2003 | Kaufman et al. | .............. | 434/262 |
| 7,187,800 B2 * | 3/2007 | Hibbard | ......................... | 382/173 |
| 2004/0015070 A1 * | 1/2004 | Liang et al. | ................... | 600/407 |
| 2004/0022438 A1 | 2/2004 | Hibbard | | |

OTHER PUBLICATIONS

Coste-Manière, È., "Robotic whole body stereotacitc radiosurgery: clinical advantages of the CyberKnife® integrated system", The International Journal of Medical Robotics +Computer Assisted Sugery, 2005, www.roboticpublications.com, 14 pages.
PCT International Search Report , International Application No. PCT/US07/07608, filed Mar. 29, 2007, mailed Mar. 4, 2008, 4 pages.
PCT Written Opinion of the International Searching Authority, International Application No. PCT/US07/07608, filed Mar. 29, 2007, mailed Mar. 4, 2008, 6 pages.
PCT International Preliminary Report on Patentability, PCT/US2007/007608 filed Mar. 29, 2007, mailed Oct. 9, 2008.
Randi J. Rost, "Using OpenGL® for Imaging," SPIE Medical Imaging 1996 Image display Conference—Feb. 10-15, Newport Beach, CA, 12 pages.

\* cited by examiner

*Primary Examiner* — Tom Y Lu
*Assistant Examiner* — Thomas A Conway
(74) *Attorney, Agent, or Firm* — Blakely, Sokoloff, Taylor & Zafman LLP

(57) ABSTRACT

A method and apparatus to delineate a volume of interest structure on a three-dimensional medical image. The apparatus includes a data storage device to store the three dimensional image and a digital processing device to delineate the volume of interest structure of the three-dimensional image.

41 Claims, 12 Drawing Sheets

DELINEATION ON THREE-DIMENSIONAL MEDICAL IMAGE

TECHNICAL FIELD

This invention relates to the field of medical imaging and, in particular, to delineating a volume of interest structure on a three-dimensional medical image.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to target regions for therapeutic, rather than necrotic, purposes. The amount of radiation utilized in radiotherapy sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment), and hyperfractionation (e.g., 30 to 45 days of treatment). For convenience, the term "radiation treatment" is used herein to include radiosurgery and/or radiotherapy, unless otherwise noted.

Traditionally, medical imaging was used to represent two-dimensional views of a patient. Modern anatomical imaging modalities such as computed tomography (CT) are able to provide an accurate three-dimensional model of a volume of a patient (e.g., skull or pathological anatomy bearing portion of the body) generated from a collection of CT slices. Each CT slice corresponds to a cross-section of the patient. These CT slices are typically obtained every 1.25 or 3 millimeters so that a set of images represents a three-dimensional model of the volume of interest.

Conventional treatment planning software packages are designed to import 3D images from a diagnostic imaging source such as magnetic resonance imaging (MRI), positron emission tomography (PET) scans, angiograms, and computerized x-ray tomography (CT) scans. During treatment planning, volumes of interest (VOI) from anatomical (e.g., CT) and/or functional imaging are used to delineate structures to be targeted or avoided with respect to the administered radiation dose. FIG. 1 illustrates a conventional contour set which may be used to define a volume of interest (VOI) structure. The contour set includes multiple image slices, including end slices and a middle slice. The volume of interest structure may be defined as a set of planar, closed polygons, within a plurality of image slices. The coordinates of the polygon vertices are defined as the x, y, and z offsets in a given unit from an image origin. Due to limited processing power, conventional treatment planning systems typically do not use every two-dimensional slice within a set. Rather, conventional treatment planning systems use linear interpolation between non-adjacent slices (e.g., every tenth slice) to minimize the time and power allocated to defining the volume of interest structure. However, linear interpolation fails to account for pathological anatomy formations such as indentations and protrusions that are only visible on the middle slices ignored and replaced by the interpolated contours.

Volume of interest structures may include target regions and critical regions. A target region is a volume of interest structure to which radiation is directed for therapeutic or surgical purposes. A critical region is a volume of interest structure for which radiation treatment is avoided. For example, a CT slice of a spinal region may include a pathological anatomy (e.g., tumor, legion, arteriovenous malformation, etc.) target region to be treated and an adjacent normal anatomy (e.g., internal organ) critical region to be avoided. The treatment planning software enables delineation of the target and critical regions on the two-dimensional CT image slices. Conventionally, a user manually delineates points on the two-dimensional image represented on a medical imaging display to generate a corresponding contour. Ideally, the volume of interest contours for all of the slices should match the corresponding target or critical region over its three-dimensional volume. Such matching is difficult due the three-dimensional nature and irregularities of the pathological and normal anatomies. For example, two-dimensional delineation is of limited applicability for complex volume of interest structures such as vascular structures.

BRIEF DESCRIPTION OF THE DRAWINGS

The present invention is illustrated by way of example, and not by way of limitation, in the figures of the accompanying drawings.

DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of a method and apparatus are described to delineate a volume of interest structure on a three-dimensional medical image. In one embodiment, the method includes receiving a three-dimensional image, including a volume of interest structure, and delineating the volume of interest structure within the three-dimensional image. A machine readable storage medium includes instructions to facilitate the operations of the method. One embodiment of the apparatus includes a data storage device to store the three dimensional image and a digital processing device to delineate the volume of interest structure of the three-dimensional image. Another embodiment of the apparatus includes means for displaying the three-dimensional image, means for distinguishing between the volume of interest structure and another anatomical structure, and means for delineating the volume of interest structure on the three-dimensional image.

Figure 1:
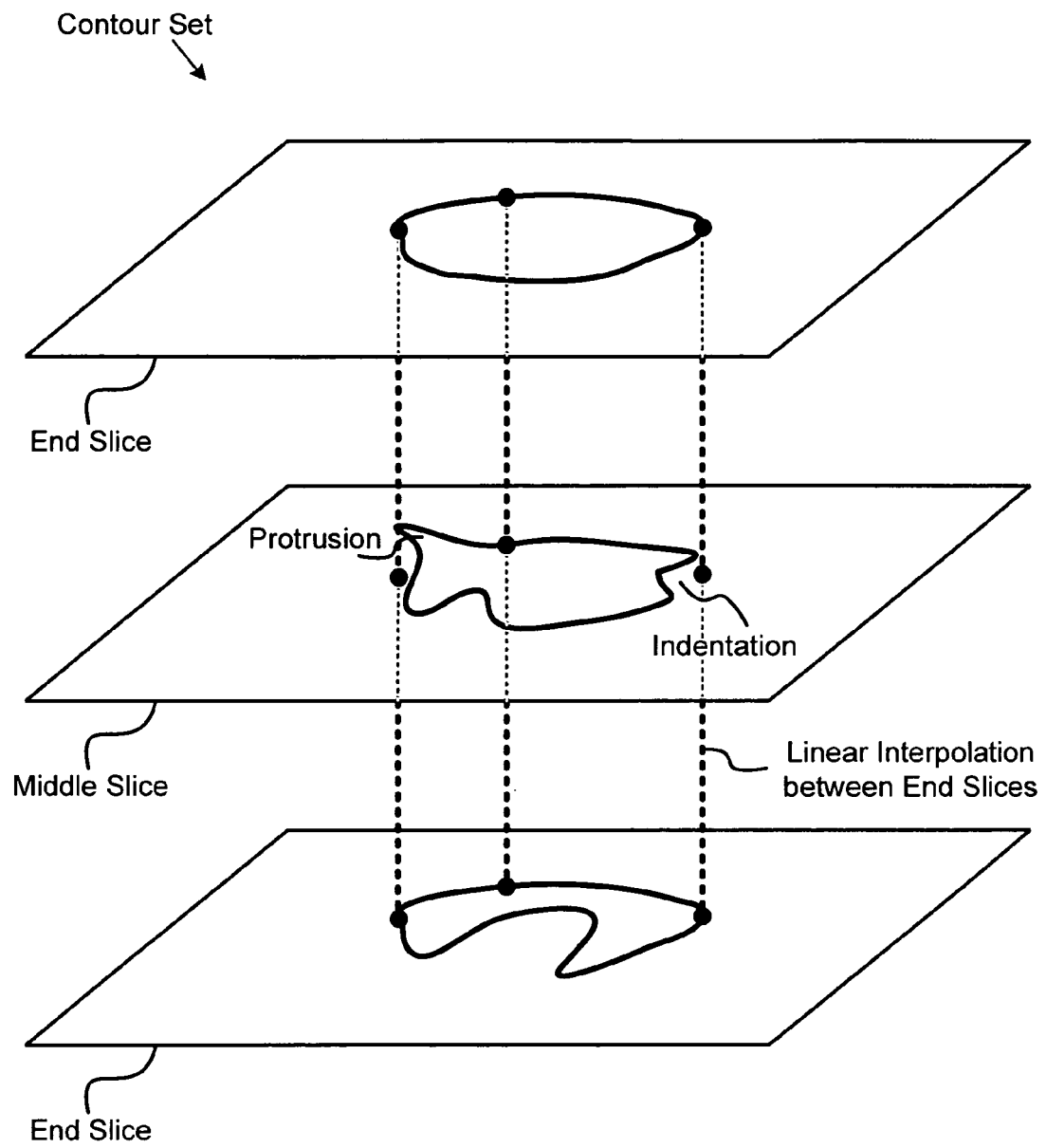
FIG. 1 illustrates a contour set to facilitate two-dimensional delineation.
Figure 2:
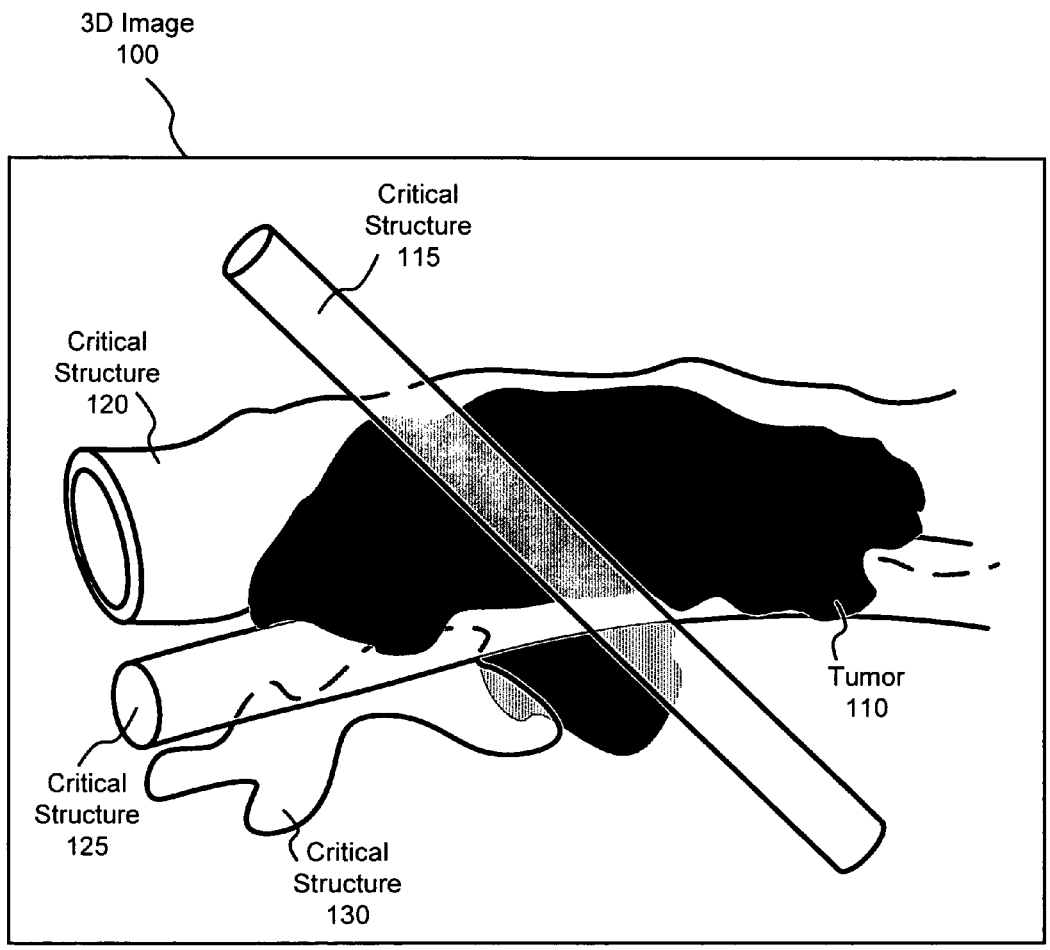
FIG. 2 illustrates one embodiment of a three-dimensional image.

FIG. 2 illustrates one embodiment of a three-dimensional image 100. The three-dimensional image 100 may be a three-dimensional CT image, a three-dimensional MRI image, or a three-dimensional image obtained through another modality. The three-dimensional image 100 may be displayed on a monitor such as a cathode ray tube (CRT) monitor, a liquid crystal display (LCD) monitor, or another type of monitor, including a medical imaging monitor.

The depicted three-dimensional image 100 includes a tumor 110 and several critical structures 115, 120, 125, and 130. The tumor 110 is representative of any type of target region. For convenience, the tumor 110 is interchangeably referred to as a target region 110, unless noted otherwise. The target region 110 also may be considered a volume of interest (VOI) structure (also referred to as simply a volume of interest). Similarly, the critical regions 115, 120, 125, and 130 may individually be designated as volume of interest structures. For convenience, reference to the critical structure 115 is representative of references to any or all of the critical regions 115, 120, 125, 130, unless noted otherwise.

Radiation treatment planning systems may use forward planning and inverse planning to determine the radiation doses for the target region 110 and critical region 115. In forward planning, a medical physicist or other user determines the radiation dose to be applied to the tumor 110 and then calculates how much radiation will be absorbed by critical structure 115 and other healthy tissue. In contrast, inverse planning allows the medical physicist or other user to independently specify a minimum dose and a maximum dose for the tumor 110 and a maximum dose for the critical region 115 and other healthy tissues. Then, the treatment planning software select the number of radiation beams, as well as the direction, distance, and energy of each radiation beam.

Delineation of the target region 10 and critical structure 115 facilitates inverse planning by independently identifying the target region 110 and the critical structure 115. During inverse planning, volume of interest (VOI) structures corresponding to the target region 110 and critical structure 115 are used to distinguish between structures to be targeted or avoided with respect to the administered radiation dose. That is, the radiation source is positioned to localize the radiation dose into a volume of interest structure that conforms as closely as possible to the target region 110 intended for radiation treatment, while avoiding exposure of the nearby critical structure 115 and other healthy tissue. Once the volume of interest structure for the target region 110 is defined, and volumes of interest structures for the critical structure 115 and soft tissue structures are specified, the responsible radiation oncologist or medical physicist specifies the minimum and maximum radiation dose to the target volume of interest structures and the maximum dose to the normal and critical volume of interest structures. The software then produces the inverse treatment plan, relying on the positional capabilities of radiation treatment system, to meet the minimum and maximum dose constraints of the treatment plan.

The two principal considerations for an effective radiation treatment plan are conformality and homogeneity. Homogeneity is the uniformity of the radiation dose over the target region 10 characterized by a dose volume histogram (DVH). An ideal dose volume histogram for a target region would be a rectangular function, where 100 percent of the prescribed dose irradiates the target region 110. An ideal dose volume histogram for a critical structure would be a zero function, where the critical structure 115 receives no radiation. Conformality is the degree to which the radiation dose matches (i.e., conforms to) the shape and extent of the target region 110 in order to avoid damage to adjacent critical structures 115. More specifically, conformality is a measure of the amount of prescription (Rx) dose within a target volume of interest structure. Conformality may be measured using a conformality index, which defines a ratio between the amount of the total volume that receives at least the prescription dose compared to the amount of the target region 110 that receives the prescription dose. Perfect conformality results in a conformality index equal to one, which indicates that only the target region 110 received the prescription dose.

In order to help a medical clinician delineate a volume of interest structure, the treatment planning software may apply a filter to the three-dimensional image 100 to assign different gray-scale values or colors and opacities to each voxel of the intensity of the various structures. For example, a tumor 110 may have an opacity that is different from a vascular critical structure 115. The opacity may be related to a frequency response of the structure resulting from the imaging radiation. In one embodiment, the three-dimensional image 100 may be displayed using different colors to indicate the different structures. One example of a filter that may be used is a window level (W/L) filter. Alternatively, other filters such as a curve-based filter may be used. Filtering offers flexibility in viewing the three-dimensional image 100 because a medical clinician may select certain filter layers to be displayed and other filter layers to be hidden. For example, the three-dimensional structure corresponding to the skin of a patient may be assigned to a filter that may be turned off and, thus, not displayed. Turning filter layers on or off within the three-dimensional image allows a user to isolate specific target regions 110 and critical structures 115 that may be used for forward and/or inverse planning delineation. In the depicted embodiment, the tumor 110 is shown in a darker shade than the critical structures 115 to illustrate that the tumor 110 may be on a different filter layer than the critical structures 115. Additionally, each critical structure may be on an individual filter layer, depending on the type of filter used and the structure characteristic used by the filter.

Figure 3:
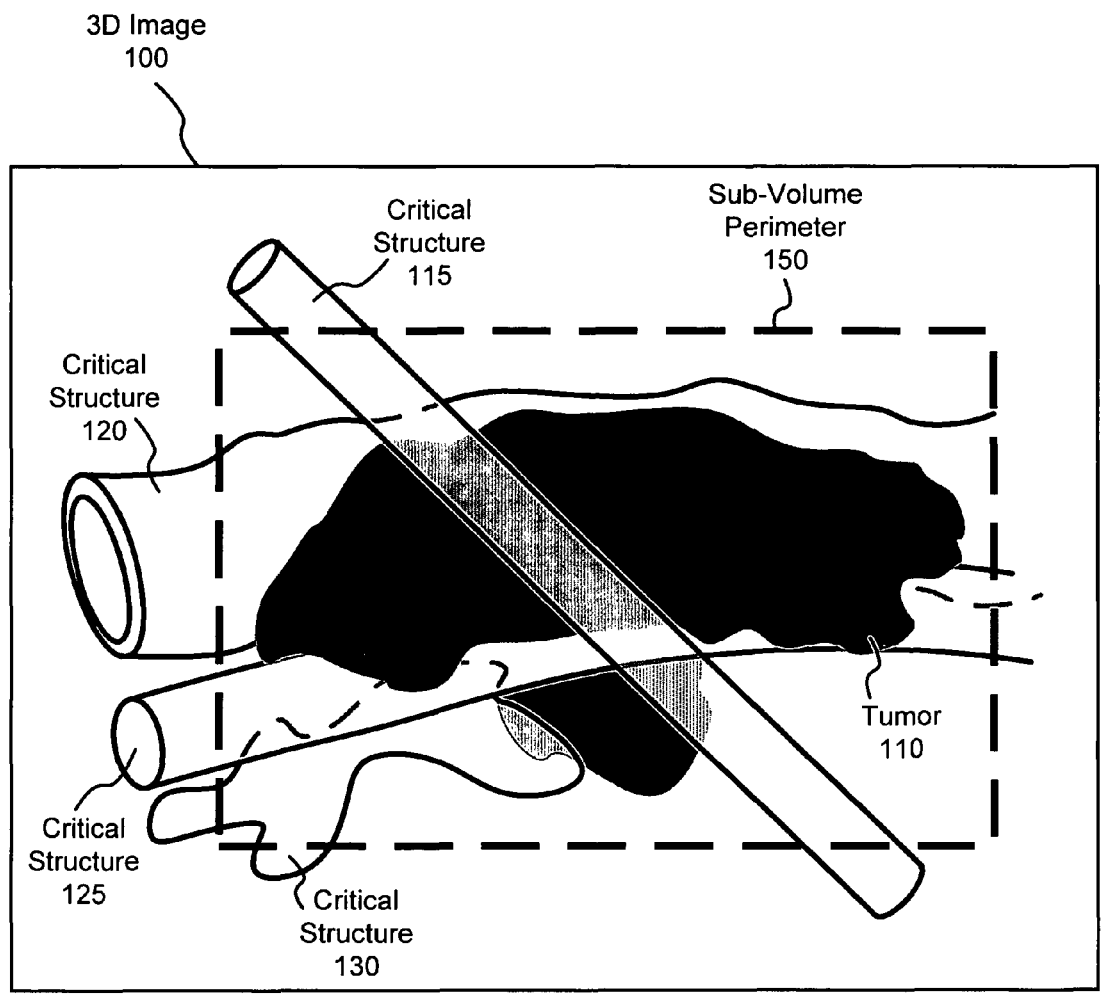
FIG. 3 illustrates one embodiment of a sub-volume perimeter on the three-dimensional image.

FIG. 3 illustrates one embodiment of a sub-volume perimeter 150 on the three-dimensional image 100. In addition to filters, the treatment planning software may allow a user to define a sub-volume perimeter 150 on the three-dimensional image 100 to display only the structures within the sub-volume perimeter 150. Other structures outside of the sub-volume perimeter 150 may be excluding from the three-dimensional image 100 displayed to the user so that the user can more readily identify certain target region 110 and critical structure 115. In one embodiment, the sub-volume perimeter 150 may be a two-dimensional shape superimposed on the three-dimensional image 100. By rotating the three-dimensional image 100 and drawing multiple two-dimensional sub-volume perimeters 150, the user may effectively limit the displayed three-dimensional image 100 to a three-dimensional sub-volume. Alternatively, the sub-volume perimeter 150 may be a three-dimensional shape such as a wire mesh sphere, rectangle, or other shape.

Figure 4:
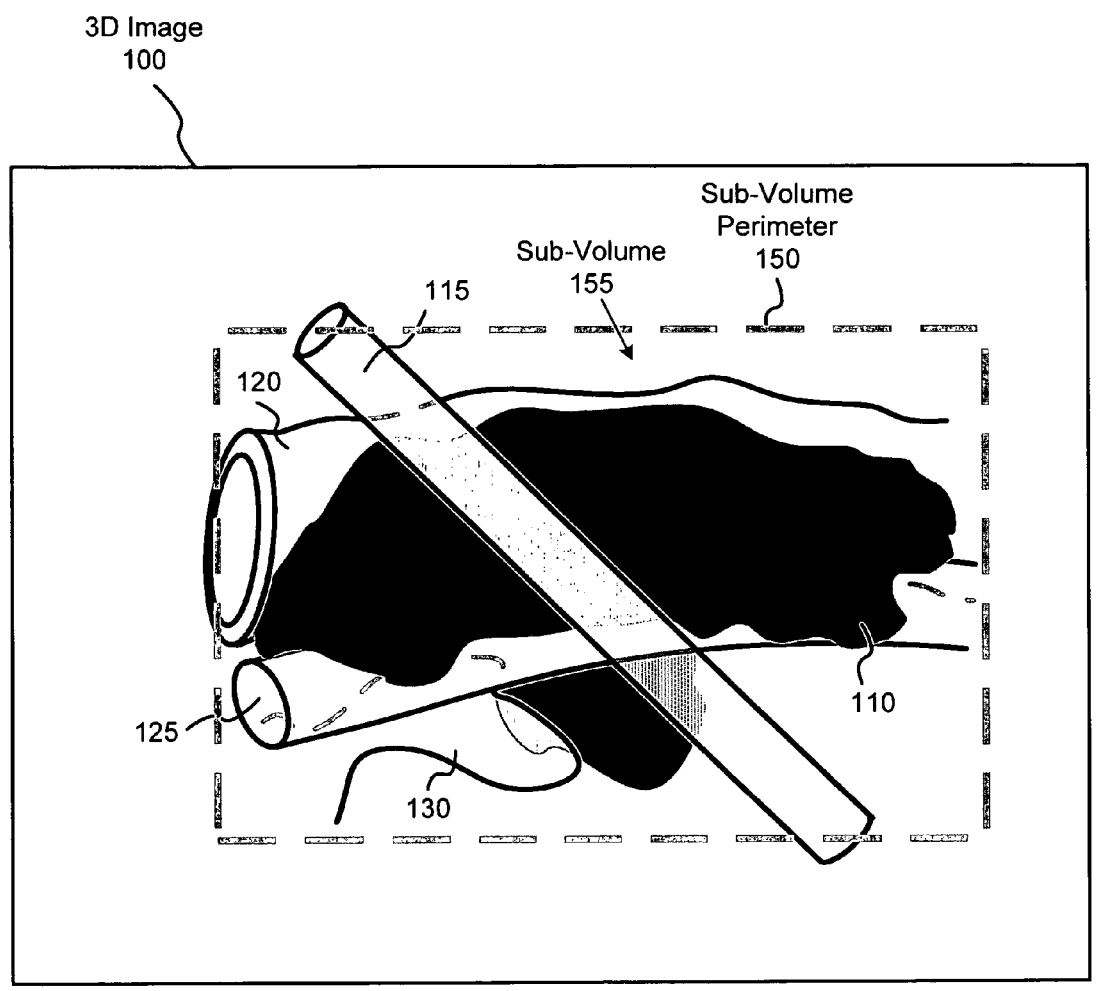
FIG. 4 illustrates one embodiment of the sub-volume on the three-dimensional image.

FIG. 4 illustrates one embodiment of a sub-volume 155 on the three-dimensional image 100. The sub-volume 155 corresponds to the three-dimensional volume defined by the sub-volume perimeter 150. One advantage of displaying only a sub-volume 155 instead of the entire volume of the three-dimensional image 100 is the ability to isolate the target region 110 and critical structure 115 from surrounding structures and tissues. Another advantage of the target sub-volume 155 is that delineation algorithms may consume less time and processor power to delineate structures within the small sub-volume 155 compared to the volume of the entire three-dimensional image 100. In this way, the filtering and sub-volume functions may allow a user to substantially isolate the target region 110 and the critical structures 115 from each other and from other structures within the volume rendering of the three-dimensional image 100 on a graphic display. This three-dimensional isolation may significantly enhance the ability and speed of a user to identify the contours of a particular volume of interest, especially in comparison with delineating separate contours on multiple two-dimensional slices.

Figure 5:
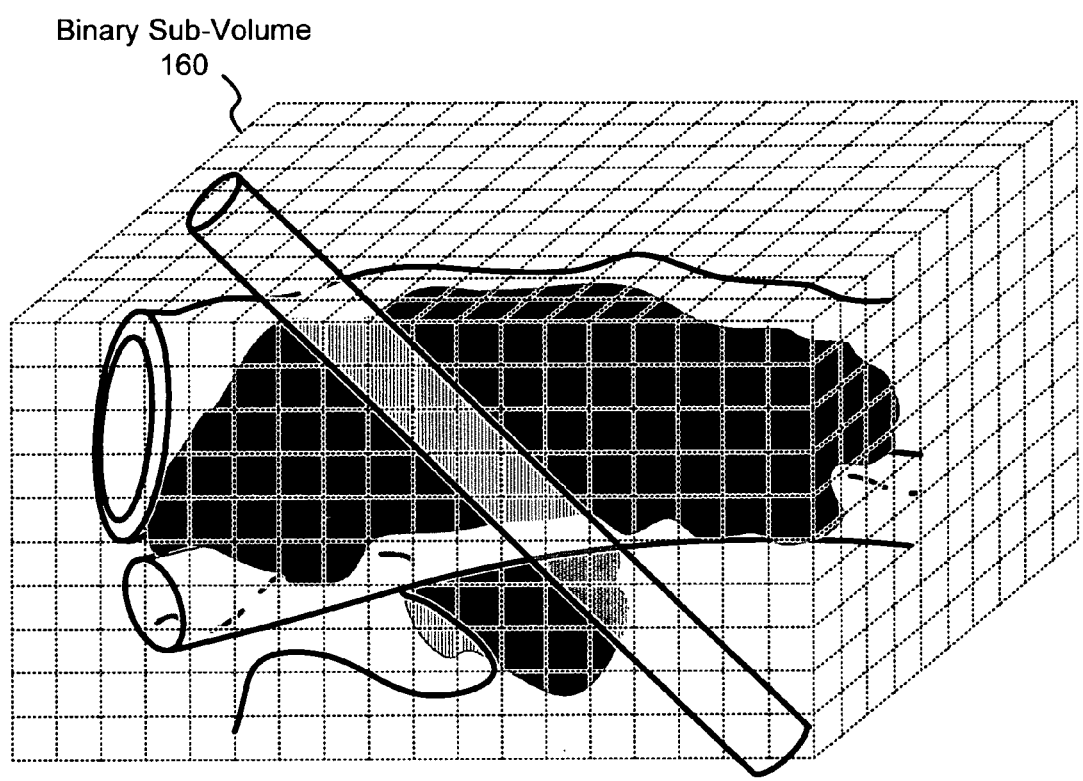
FIG. 5 illustrates one embodiment of a binary sub-volume corresponding to the sub-volume on the three-dimensional image.

FIG. 5 illustrates one embodiment of a binary sub-volume 160 corresponding to the sub-volume 155 on the three-dimensional image 100. The binary sub-volume 160 is one representation of the sub-volume 155 that assigns at least a binary value to each volume element, or voxel, within the sub-volume 155. In one embodiment, a voxel may represent a volume having dimensions of approximately 0.5 by 0.5 by 1.25 millimeters. Every voxel is associated with a word having 32 bits (i.e., 4 bytes). Alternatively, another number of bits may be associated with each voxel. One or more bits of the word may be used to indicate if a voxel belongs to the binary sub-volume 160. Other bits of the word may be used to indicate if the corresponding voxel belongs to a particular structure such as a volume of interest structure, as described below. For each structure, a given bit value may be either a "1" or a "0" to indicate whether that particular voxel is part of the volume of interest structure corresponding to that bit. For example, with a 32-bit word, each voxel may be designated as belonging to as many as 32 volume of interest structures.

Figure 6:
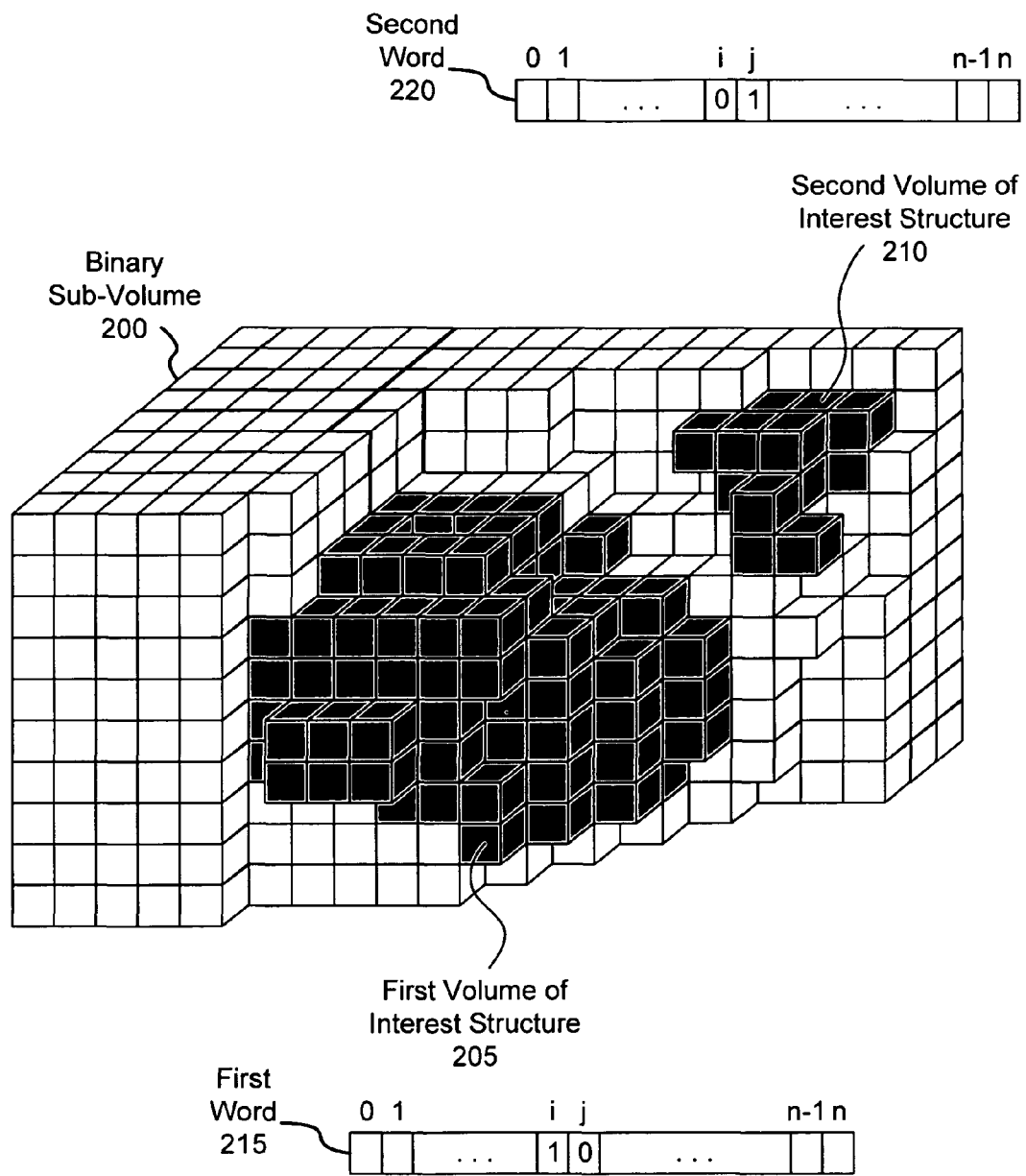
FIG. 6 illustrates another embodiment of the binary sub-volume with binary masks of first and second volume of interest structures.

FIG. 6 illustrates another embodiment of the binary sub-volume 200 with binary masks of first and second volume of interest structures 205 and 210. As an example, the first volume of interest structure 205 may represent a target region 110. The second volume of interest structure 210 may represent a critical structure 115. Each shaded cuboid illustrates a voxel that belongs to one of the first or second volume of interest structures 205 and 210, while the non-shaded cuboids represent voxels that do not belong to the first or second volume of interest structures 205 and 210.

The illustrated first word 215 is representative of words corresponding to voxels within the first volume of interest structure 205. The i-th bit of the first word 215 indicates whether or not the corresponding voxel belongs to the first volume of interest structure 205. Therefore, all of the voxels associated with the first volume of interest structure 205 have a "1" bit value in the i-th bit. All of the voxels not associated with the first volume of interest structure 205 have a "0" bit value in the i-th bit. Similarly, the illustrated second word 220 is representative of words corresponding to voxels within the second volume of interest structure 210. The j-th bit of the second word 220 indicates whether or not the corresponding voxel belongs to the second volume of interest structure 210. Therefore, all of the voxels associated with the second volume of interest structure 210 have a "1" bit value in the j-th bit, and all of the voxels not associated with the second volume of interest structure 210 have "0" bit value in the j-th bit. In some situations, a single voxel may belong to multiple volume of interest structures, in which case several bits within the corresponding word for that voxel may have a "1" bit value. Otherwise, if a voxel within the binary sub-volume 200 is not associated with any volume of interest structures 205 or 210 within the binary sub-volume 200, then all of the bits for the word corresponding to that voxel will have "0" bit values. In some embodiments, the binary sub-volume 200 or individual binary volume of interest structures 205 or 210 may be referred to as bit masks or binary masks.

Figure 7:
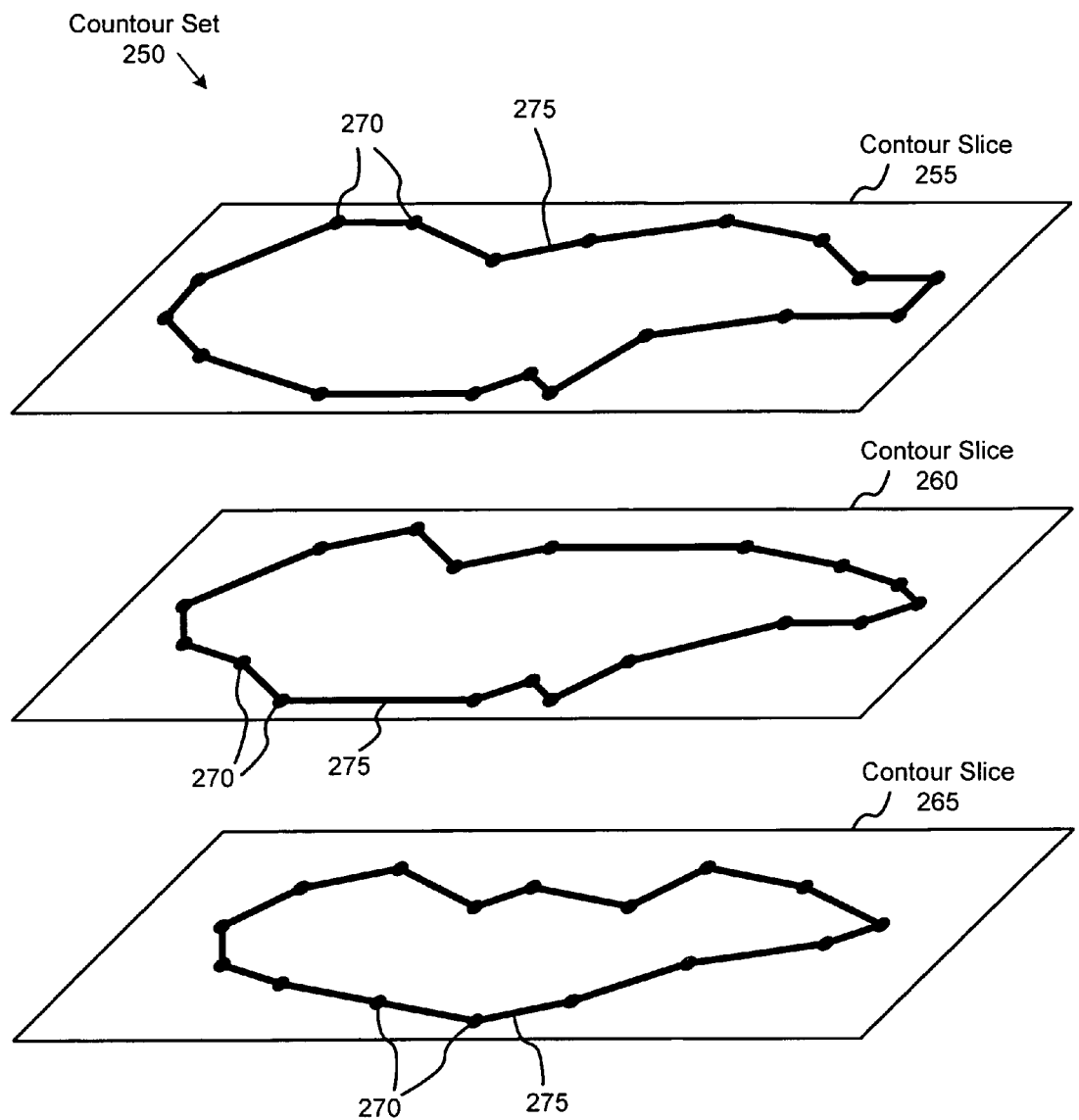
FIG. 7 illustrates one embodiment of a contour set derived from the binary sub-volume.

FIG. 7 illustrates one embodiment of a contour set 250 derived from the binary sub-volume 160. The contour set 250 includes several contour slices 255, 260, and 265. For convenience, reference to the contour slice 255 is representative of all of the contour slices 255, 260, and 265, unless noted otherwise. Each contour slice 255 may correspond to a layer of the binary sub-volume 160 shown in FIG. 5. Each contour slice 255 shows a contour of at least one of the volume of interest structures 205 and 210 within the binary sub-volume 160. Although one contour is shown per contour slice 255, other embodiments, may include multiple contours per contour slice 255. Alternatively, each contour set 250 may correspond to a single volume of interest structure 205 and 210.

In one embodiment, the individual contours are formed by identifying various points 270 on the perimeter of the volume of interest structure 205 or 210. The identified points are then connected using at least one linear or curvilinear approximation 270. In another embodiment, the treatment planning software may identify all of the voxels on the perimeter of a volume of interest structure 205 or 210. In other words, the actual voxels defining the boundary of a volume of interest structure may be used to derive the contour slices 255.

Figure 8:
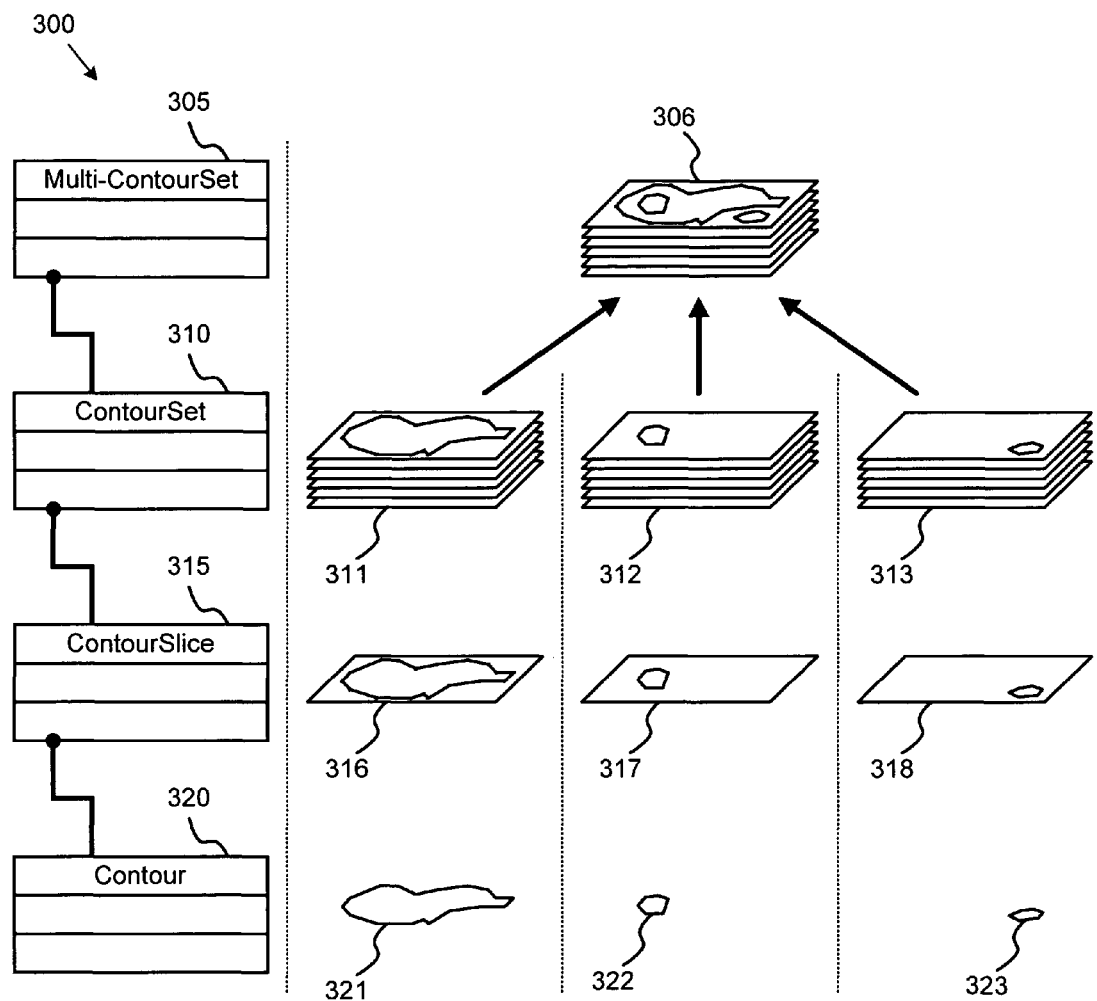
FIG. 8 illustrates one embodiment of a unified modeling language (UML) representation of a multi-contour set.

FIG. 8 illustrates one embodiment of a unified modeling language (UML) representation 300 of a multi-contour set 305. The unified modeling language is a graphical language for visualizing, specifying, constructing, and documenting artifacts of a software-intensive system. The unified modeling language offers a standard way to write programming language statements, database schemas, and software components. A more detailed discussion of the unified modeling language is not provided herein because the unified modeling language is known in the art.

The depicted UML representation 300 includes four tiers of data structures: a multi-contour set data structure 305, one or more contour set data structures 310, one or more contour slice data structures 315, and one or more contour data structures 320. For each tier, representative slices and/or contours are shown in corresponding arrangements, as described below. The contour set tier 310, in particular, corresponds to a given volume of interest structure 205, as described above in regard to FIG. 7.

The multi-contour data structure 305 is a compilation of all of the volume of interest structures 205 within a sub-volume 150. A corresponding multi-contour set 306 is representative of all of the slices of all of the volume of interest structures 205. Several contour set data structures 310 may be used to form the multi-contour set data structure 305. Each contour set 311-313 includes several slices for a single volume of interest structure 205. The volume of interest structures 205 may be target regions 110, critical structures 115, other tissues, dose isocontours, or other delineations identified by a user such as a medical clinician. In the illustrated example, three contour sets 311-313 make up the multi-contour set 306. Although three contour sets 311-313 are shown, other multi-contour sets 306 may include fewer or more individual contour sets 311-313. One or more contour slice data structures 315 make up the contour set data structure 310. Individual contour slices 316-318 are shown for the corresponding contour sets 311-313. For each of the contour slice data structures 315, corresponding contour data structures 320 may be identified. For example, each of the contour slices 316-318 has a corresponding contour 321-323.

A series of Boolean operators may be used to merge the contour set data structures 310 to describe the multi-contour data structure 305. For example, depending on the characteristics of a given volume of interest structure 205, the multi-contour set may be defined using the Boolean OR operator ($\cup$) or the AND operator ($\cap$). For example, where a first VOI structure represents the target region 110 and a second VOI structure represents a hole or cavity within the target region 110, the resulting multi-contour set 306 may be represented by the following equation:

$$VOI = VOI_1 \cap \overline{VOI_2}$$

Other variations of Boolean algorithms may be devised to account for critical structures 115 and other anatomical features that may be considered in regard to radiation treatment. For example, although the above example includes a single cavity, other algorithms may describe target regions 110 having multiple cavities.

Additionally, the merged contour sets 311-313 do not all need to be in the same plane as each other. For example, a solid region defined in the axial direction may be merged with a cavity defined in the sagittal direction. Some anatomical locations are much better viewed in one plane than in another plane. As such, it may be desirable to utilize images taken in different planes. In addition, the Boolean operations discussed above may also be used to define a volume of interest having a branch, a protrusion, an indentation, or another non-linear characteristic.

Figure 9:
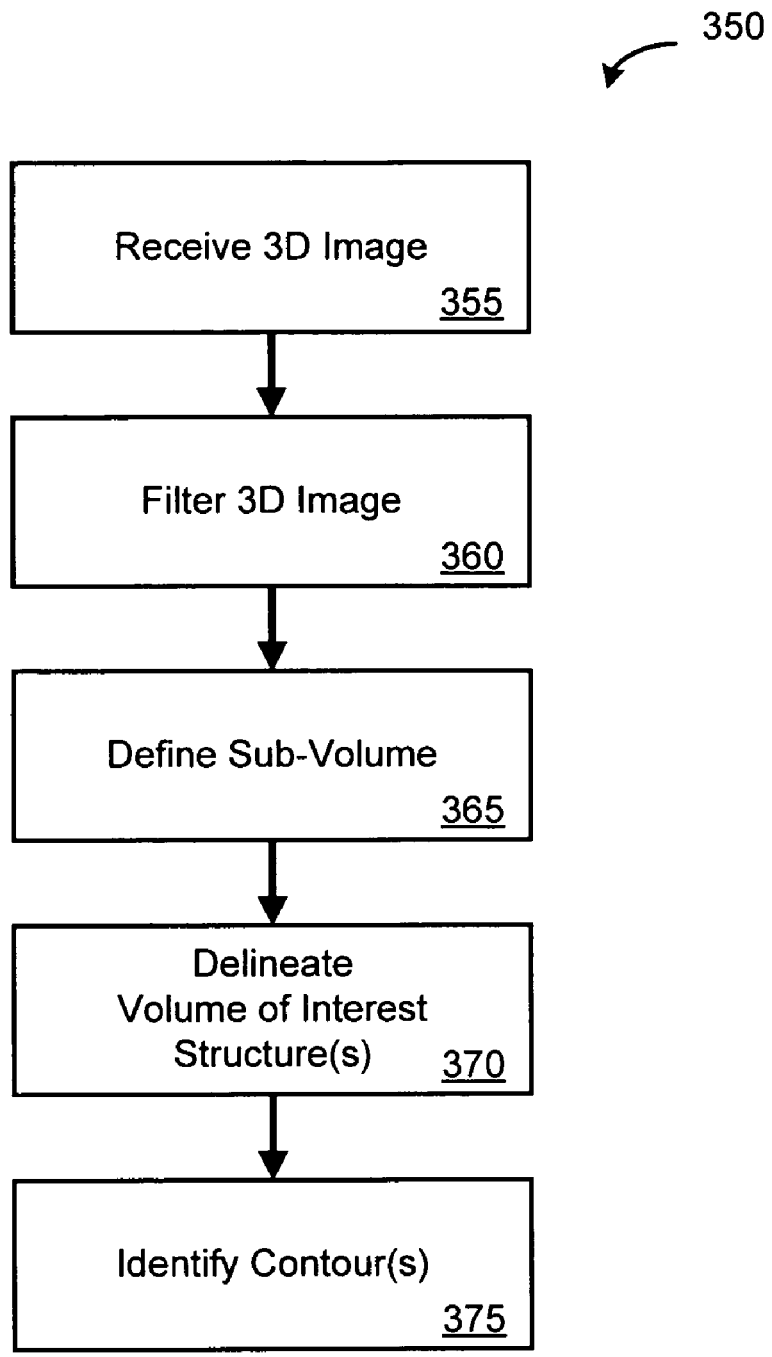
FIG. 9 illustrates one embodiment of a delineation method.

FIG. 9 illustrates one embodiment of a delineation method 350. The depicted delineation method 350 may be implemented on a treatment planning system in a radiation treatment system, as described below. The delineation method 350 begins and the treatment planning system receives 355 a three-dimensional image such as the three-dimensional image 100 of FIG. 2. The three-dimensional image includes a volume of interest structure such as the volume of interest structures 110 and 115. The three-dimensional image also may include critical structures, tissues, and other anatomical features.

The treatment planning system then filters 360 the three-dimensional image to distinguish between different types of structures in the three-dimensional image. In one embodiment, a user directs the treatment planning system to filter the three-dimensional image by making a selection on the graphical display of the treatment planning system. The user then defines 365 a sub-volume of the three-dimensional image. Alternatively, the user may define 365 the sub-volume prior to filtering 360 the three-dimensional image so that the treatment planning system 360 only filters the structures within the defined sub-volume. In one embodiment, the user may define the sub-volume on the graphical display using a two- or three-dimensional sub-volume perimeter.

The treatment planning system then delineates the volume of interest structure within the three-dimensional image. In one embodiment, the user may provide a seed value such as a value corresponding to the intensity of the target region 110. The treatment planning system then finds all of the voxels within the filtered sub-volume corresponding to the identified volume of interest structure. In this way, every voxel that is associated with the indicated volume of interest structure within the sub-volume may be identified (e.g., in the bit words corresponding to the voxels) as belonging to the specified volume of interest structure. Additionally, the treatment planning system may identify other voxels associated with other volume of interest structures. After the treatment planning system delineates 370 the volume of interest structures, the treatment planning system automatically identifies the two- and three-dimensional contours of the delineated volume of interest structures. The illustrated delineation method 350 then ends.

Figure 10:
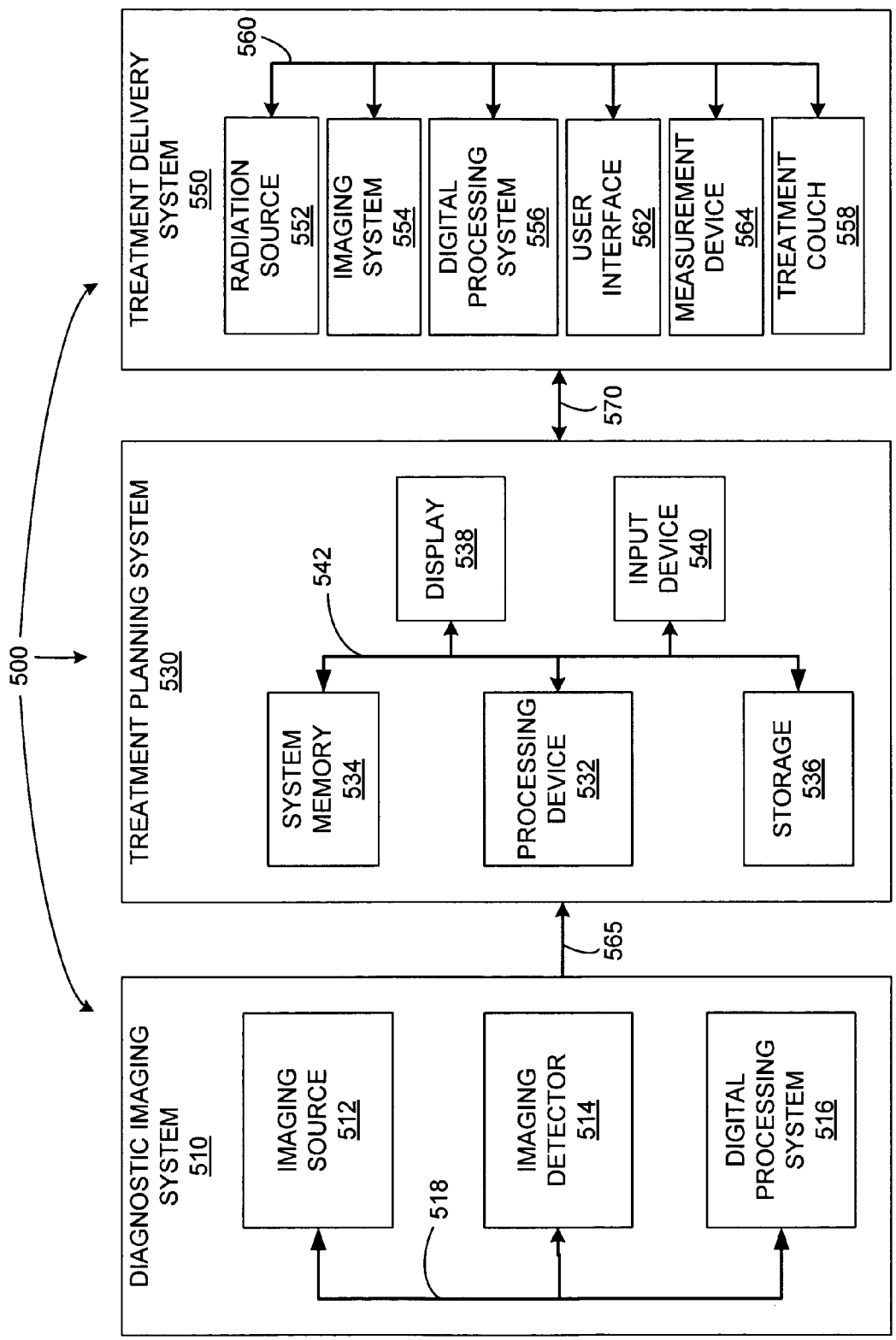
FIG. 10 illustrates one embodiment of a treatment system that may be used to perform radiation treatment in which an embodiment of the present invention may be implemented.

FIG. 10 illustrates one embodiment of a treatment system 500 that may be used to perform radiation treatment in which features of the present invention may be implemented. The depicted treatment system 500 includes a diagnostic imaging system 510, a treatment planning system 530, and a treatment delivery system 550. In other embodiments, the treatment system 500 may include fewer or more component systems.

The diagnostic imaging system 510 is representative of any system capable of producing medical diagnostic images of a volume of interest (VOI) in a patient, which images may be used for subsequent medical diagnosis, treatment planning, and/or treatment delivery. For example, the diagnostic imaging system 510 may be a computed tomography (CT) system, a magnetic resonance imaging (MRI) system, a positron emission tomography (PET) system, an ultrasound system, or another similar imaging system. For ease of discussion, any specific references herein to a particular imaging system such as a CT x-ray imaging system is representative of the diagnostic imaging system 510, generally, and does not preclude other imaging modalities, unless noted otherwise.

The illustrated diagnostic imaging system 510 includes an imaging source 512, an imaging detector 514, and a digital processing system 516. The imaging source 512, imaging detector 514, and digital processing system 516 are coupled to one another via a communication channel 518 such as a bus. In one embodiment, the imaging source 512 generates an imaging beam (e.g., x-rays, ultrasonic waves, radio frequency waves, etc.) and the imaging detector 514 detects and receives the imaging beam. Alternatively, the imaging detector 514 may detect and receive a secondary imaging beam or an emission stimulated by the imaging beam from the imaging source (e.g., in an MRI or PET scan). In one embodiment, the diagnostic imaging system 510 may include two or more diagnostic imaging sources 512 and two or more corresponding imaging detectors 514. For example, two x-ray sources 512 may be disposed around a patient to be imaged, fixed at an angular separation from each other (e.g., 90 degrees, 45 degrees, etc.) and aimed through the patient toward corresponding imaging detectors 514, which may be diametrically opposed to the imaging sources 514. A single large imaging detector 514, or multiple imaging detectors 514, also may be illuminated by each x-ray imaging source 514. Alternatively, other numbers and configurations of imaging sources 512 and imaging detectors 514 may be used.

The imaging source 512 and the imaging detector 514 are coupled to the digital processing system 516 to control the imaging operations and process image data within the diagnostic imaging system 510. In one embodiment, the digital processing system 516 may communicate with the imaging source 512 and the imaging detector 514. Embodiments of the digital processing system 516 may include one or more general-purpose processors (e.g., a microprocessor), special purpose processors such as a digital signal processor (DSP), or other type of devices such as a controller or field programmable gate array (FPGA). The digital processing system 516 also may include other components (not shown) such as memory, storage devices, network adapters, and the like. In one embodiment, the digital processing system 516 generates digital diagnostic images in a standard format such as the Digital Imaging and Communications in Medicine (DICOM) format. In other embodiments, the digital processing system 516 may generate other standard or non-standard digital image formats.

Additionally, the digital processing system 516 may transmit diagnostic image files such as DICOM files to the treatment planning system 530 over a data link 560. In one embodiment, the data link 560 may be a direct link, a local area network (LAN) link, a wide area network (WAN) link such as the Internet, or another type of data link. Furthermore, the information transferred between the diagnostic imaging system 510 and the treatment planning system 530 may be either pulled or pushed across the data link 560, such as in a remote diagnosis or treatment planning configuration. For example, a user may utilize embodiments of the present invention to remotely diagnose or plan treatments despite the existence of a physical separation between the system user and the patient.

The illustrated treatment planning system 530 includes a processing device 532, a system memory device 534, an electronic data storage device 536, a display device 538, and an input device 540. The processing device 532, system memory 534, storage 536, display 538, and input device 540 may be coupled together by one or more communication channel 542 such as a bus.

The processing device 532 receives and processes image data. The processing device 532 also processes instructions and operations within the treatment planning system 530. In certain embodiments, the processing device 532 may include one or more general-purpose processors (e.g., a microprocessor), special purpose processors such as a digital signal processor (DSP), or other types of devices such as a controller or field programmable gate array (FPGA).

In particular, the processing device 532 may be configured to execute instructions for performing treatment operations discussed herein. For example, the processing device 532 may identify a non-linear path of movement of a target within a patient and develop a non-linear model of the non-linear path of movement. In another embodiment, the processing device 532 may develop the non-linear model based on a plurality of position points and a plurality of direction indicators. In another embodiment, the processing device 532 may generate a plurality of correlation models and select one of the plurality of models to derive a position of the target. Furthermore, the processing device 532 may facilitate other diagnosis, planning, and treatment operations related to the operations described herein.

In one embodiment, the system memory 534 may include random access memory (RAM) or other dynamic storage devices. As described above, the system memory 534 may be coupled to the processing device 532 by the communication channel 542. In one embodiment, the system memory 534 stores information and instructions to be executed by the processing device 532. The system memory 534 also may be used for storing temporary variables or other intermediate information during execution of instructions by the processing device 532. In another embodiment, the system memory 534 also may include a read only memory (ROM) or other static storage device for storing static information and instructions for the processing device 532.

In one embodiment, the storage 536 is representative of one or more mass storage devices (e.g., a magnetic disk drive, tape drive, optical disk drive, etc.) to store information and instructions. The storage 536 and/or the system memory 534 also may be referred to as machine readable media. In a specific embodiment, the storage 536 may store instructions to perform the modeling operations discussed herein. For example, the storage 536 may store instructions to acquire and store data points, acquire and store images, identify non-linear paths, develop linear and/or non-linear correlation models, select a correlation model from a plurality of models, and so forth. In another embodiment, the storage 536 may include one or more databases.

In one embodiment, the display 538 may be a cathode ray tube (CRT) display, a liquid crystal display (LCD), or another type of display device. The display 538 displays information (e.g., a two-dimensional or three-dimensional representation of the VOI) to a user. The input device 540 may include one or more user interface devices such as a keyboard, mouse, trackball, or similar device. The input device(s) 540 may also be used to communicate directional information, to select commands for the processing device 532, to control cursor movements on the display 538, and so forth.

Although one embodiment of the treatment planning system 530 is described herein, the described treatment planning system 530 is only representative of an exemplary treatment planning system 530. Other embodiments of the treatment planning system 530 may have many different configurations and architectures and may include fewer or more components. For example, other embodiments may include multiple buses, such as a peripheral bus or a dedicated cache bus. Furthermore, the treatment planning system 530 also may include Medical Image Review and Import Tool (MIRIT) to support DICOM import so that images can be fused and targets delineated on different systems and then imported into the treatment planning system 530 for planning and dose calculations. In another embodiment, the treatment planning system 530 also may include expanded image fusion capabilities that allow a user to plan treatments and view dose distributions on any one of various imaging modalities such as MRI, CT, PET, and so forth. Furthermore, the treatment planning system 530 may include one or more features of convention treatment planning systems.

In one embodiment, the treatment planning system 530 may share a database on the storage 536 with the treatment delivery system 550 so that the treatment delivery system 550 may access the database prior to or during treatment delivery. The treatment planning system 530 may be linked to treatment delivery system 550 via a data link 570, which may be a direct link, a LAN link, or a WAN link, as discussed above with respect to data link 560. Where LAN, WAN, or other distributed connections are implemented, any of components of the treatment system 500 may be in decentralized locations so that the individual systems 510, 530, 550 may be physically remote from one other. Alternatively, some or all of the functional features of the diagnostic imaging system 510, the treatment planning system 530, or the treatment delivery system 550 may be integrated with each other within the treatment system 500.

The illustrated treatment delivery system 550 includes a radiation source 552, an imaging system 554, a digital processing system 556, and a treatment couch 558. The radiation source 552, imaging system 554, digital processing system 556, and treatment couch 558 may be coupled to one another via one or more communication channel 560. One example of a treatment delivery system 550 is shown and described in more detail with reference to FIG. 11.

In one embodiment, the radiation source 552 is a therapeutic or surgical radiation source 552 to administer a prescribed radiation dose to a target volume in conformance with a treatment plan. For example, the target volume may be an internal organ, a tumor, a region. For convenience, reference herein to the target volume or a target refers to any whole or partial organ, tumor, region, or other delineated volume that is the subject of a treatment plan.

In one embodiment, the imaging system 554 of the treatment delivery system 550 captures intra-treatment images of a patient volume, including the target volume, for registration or correlation with the diagnostic images described above in order to position the patient with respect to the radiation source. Similar to the diagnostic imaging system 510, the imaging system 554 of the treatment delivery system 550 may include one or more sources and one or more detectors.

The treatment delivery system 550 also may include a digital processing system 556 to control the radiation source 552, the imaging system 554, and a treatment couch 558, which is representative of any patient support device. The digital processing system 556 may include one or more general-purpose processors (e.g., a microprocessor), special purpose processors such as a digital signal processor (DSP), or other devices such as a controller or field programmable gate array (FPGA). Additionally, the digital processing system 556 may include other components (not shown) such as memory, storage devices, network adapters, and the like.

Figure 11:
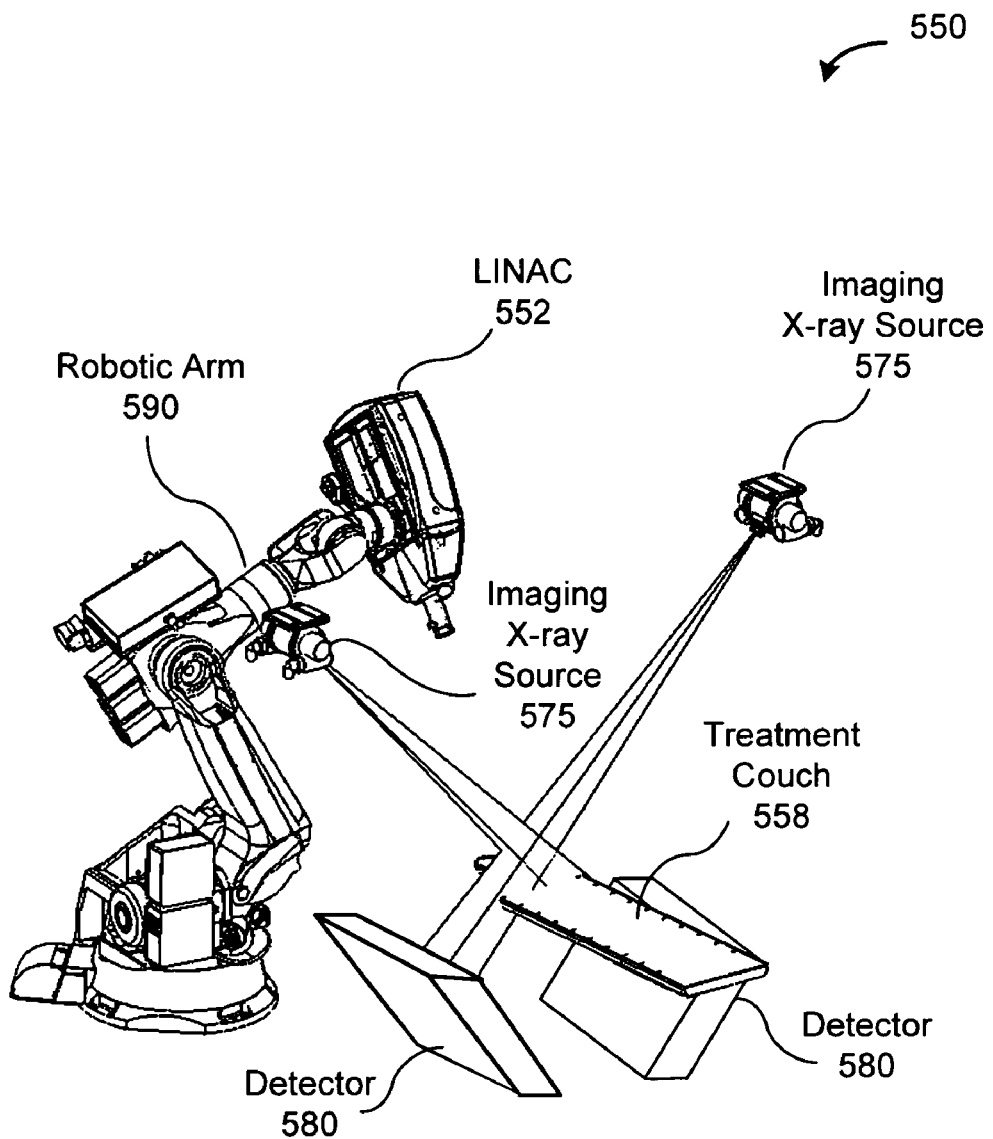
FIG. 11 is a schematic block diagram illustrating one embodiment of a treatment delivery system.

FIG. 11 is a schematic block diagram illustrating one embodiment of a treatment delivery system 550. The depicted treatment delivery system 550 includes a radiation source 552, in the form of a linear accelerator (LINAC) 552, and a treatment couch 558, as described above. The treatment delivery system 550 also includes multiple imaging x-ray sources 575 and detectors 580. The two x-ray sources 575 may be nominally aligned to project imaging x-ray beams through a patient from at least two different angular positions (e.g., separated by 90 degrees, 45 degrees, etc.) and aimed through the patient on the treatment couch 558 toward the corresponding detectors 580. In another embodiment, a single large imager may be used to be illuminated by each x-ray imaging source 575. Alternatively, other quantities and configurations of imaging sources 575 and detectors 580 may be used. In one embodiment, the treatment delivery system 550 may be an image-guided, robotic-based radiation treatment system (e.g., for performing radiosurgery) such as the CYBERKNIFE® system developed by Accuray Incorporated of Sunnyvale, Calif.

In the illustrated embodiment, the LINAC 552 is mounted on a robotic arm 590. The robotic arm 590 may have multiple (e.g., 5 or more) degrees of freedom in order to properly position the LINAC 552 to irradiate a target such as a pathological anatomy with a beam delivered from many angles in an operating volume around the patient. The treatment implemented with the treatment delivery system 550 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. In one embodiment, the treatment delivery system 550 delivers radiation beams according to the treatment plan without fixing the patient to a rigid, external frame to register the intra-operative position of the target volume with the position of the target volume during the pre-operative treatment planning phase.

As described above, the digital processing system 556 may implement algorithms to register images obtained from the imaging system 554 with pre-operative treatment planning images obtained from the diagnostic imaging system 510 in order to align the patient on the treatment couch 558 within the treatment delivery system 550. Additionally, these images may be used to precisely position the radiation source 552 with respect to the target volume or target.

In one embodiment, the treatment couch 558 may be coupled to second robotic arm (not shown) having multiple degrees of freedom. For example, the second arm may have five rotational degrees of freedom and one substantially vertical, linear degree of freedom. Alternatively, the second arm may have six rotational degrees of freedom and one substantially vertical, linear degree of freedom. In another embodiment, the second arm may have at least four rotational degrees of freedom. Additionally, the second arm may be vertically mounted to a column or wall, or horizontally mounted to pedestal, floor, or ceiling. Alternatively, the treatment couch 558 may be a component of another mechanism, such as the AXUM® treatment couch developed by Accuray Incorporated of Sunnyvale, Calif. In another embodiment, the treatment couch 558 may be another type of treatment table, including a conventional treatment table.

Although one exemplary treatment delivery system 550 is described above, the treatment delivery system 550 may be another type of treatment delivery system. For example, the treatment delivery system 550 may be a gantry based (isocentric) intensity modulated radiotherapy (IMRT) system, in which a radiation source 552 (e.g., a LINAC) is mounted on the gantry in such a way that it rotates in a plane corresponding to an axial slice of the patient. Radiation may be delivered from several positions on the circular plane of rotation. In another embodiment, the treatment delivery system 550 may be a stereotactic frame system such as the GAM-MAKNIFE®, available from Elekta of Sweden.

Figure 12:
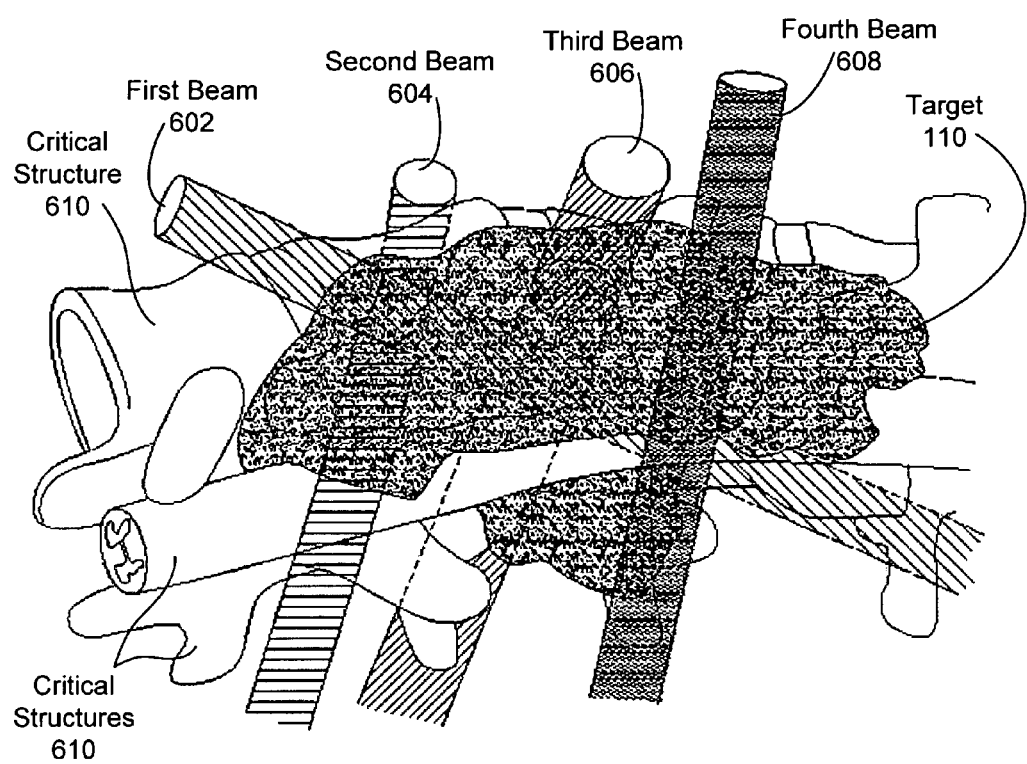
FIG. 12 illustrates a three-dimensional perspective view of a radiation treatment process.

FIG. 12 illustrates a three-dimensional perspective view of a radiation treatment process. In particular, FIG. 12 depicts several radiation beams directed at a target region 110. In one embodiment, the target region 110 may be representative of an internal organ, a region within a patient, a pathological anatomy such as a tumor or lesion, or another type of object or area of a patient. The target region 110 also may be referred to herein as a target, a target volume, and so forth, but each of these references is understood to refer generally to the target 110, unless indicated otherwise.

The illustrated radiation treatment process includes a first radiation beam 602, a second radiation beam 604, a third radiation beam 606, and a fourth radiation beam 608. Although four radiation beams 602-608 are shown, other embodiments may include fewer or more radiation beams. For convenience, reference to one radiation beam 602 is representative of all of the radiation beams 602-608, unless indicated otherwise. Additionally, the treatment sequence for application of the radiation beams 602-608 may be independent of their respective ordinal designations.

In one embodiment, the four radiation beams 602 are representative of beam delivery based on conformal planning, in which the radiation beams 602 pass through or terminate at various points within target region 110. In conformal planning, some radiation beams 602 may or may not intersect or converge at a common point in three-dimensional space. In other words, the radiation beams 602 may be non-isocentric in that they do not necessarily converge on a single point, or isocenter. However, the radiation beams 602 may wholly or partially intersect at the target 10 with one or more other radiation beams 602.

In another embodiment, the intensity of each radiation beam 602 may be determined by a beam weight that may be set by an operator or by treatment planning software. The individual beam weights may depend, at least in part, on the total prescribed radiation dose to be delivered to target region 110, as well as the cumulative radiation dose delivered by some or all of the radiation beams 602. For example, if a total prescribed dose of 3500 cGy is set for the target region 110, the treatment planning software may automatically predetermine the beam weights for each radiation beam 602 in order to balance conformality and homogeneity to achieve that prescribed dose. Conformality is the degree to which the radiation dose matches (conforms to) the shape and extent of the target 10 (e.g., tumor) in order to avoid damage to critical adjacent structures. Homogeneity is the uniformity of the radiation dose over the volume of the target region 110. The homogeneity may be characterized by a dose volume histogram (DVH), which ideally may be a rectangular function in which 100 percent of the prescribed dose would be over the volume of the target region 110 and would be zero everywhere else.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by treatment planning software, such as the application of a beam (e.g., radiation, acoustic, etc.).

Embodiments of the present invention include various operations, which will are described herein. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

The digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple microengines. Additionally, the digital processing device may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising: receiving, by a treatment planning system, a three-dimensional image, wherein the three-dimensional image includes a volume of interest structure; and interacting directly with the 3D image by a user, with a user input device of the treatment planning system, identifying one or more locations within the three-dimensional image to delineate, at least in part, the volume of interest structure within the three-dimensional image.

2. The method of claim 1, wherein the volume of interest structure is represented by a volume rendering on the three-dimensional image.

3. The method of claim 1, further comprising identifying a set of voxels from the three-dimensional image to provide a binary description of the volume of interest structure.

4. The method of claim 3, further comprising identifying a contour of the volume of interest structure based on the set of voxels.

5. The method of claim 4, further comprising saving a representation of the contour of the volume of interest structure to a contour set, wherein the contour set comprises the contour and a plurality of other two-dimensional contours of the volume of interest structure.

6. The method of claim 5, further comprising saving the contour set to a multi-contour set, wherein the multi-contour set comprises the contour set of the volume of interest structure and at least one other contour set of a corresponding at least one other volume of interest structures.

7. The method of claim 1, wherein the volume of interest structure comprises a target structure or a critical structure.

8. The method of claim 1, further comprising applying a filter to the three-dimensional image to distinguish the volume of interest structure from another structure.

9. The method of claim 8, further comprising associating an identifier with the volume of interest structure, wherein the identifier comprises a luminance value or a color value.

10. The method of claim 8, further comprising associating an identifier with the volume of interest structure, wherein the identifier comprises an opacity value.

11. The method of claim 1, further comprising defining a sub-volume of the three-dimensional image, wherein the sub-volume is inclusive of the volume of interest structure.

12. The method of claim 11, wherein defining the sub-volume comprises identifying a surface of the sub-volume.

13. The method of claim 11, wherein defining the sub-volume comprises identifying a portion of the three-dimensional image to be excluded from the sub-volume.

14. The method of claim 1, wherein delineating of the volume of interest structure within the three-dimensional image is performed by a user using an input device of the treatment planning system and a graphical display, displaying the three-dimensional image, of the treatment planning system.

15. The method of claim 1, wherein delineating the volume of interest structure is performed after at least one of filtering the three-dimensional image by a user using an input device of the treatment planning system or defining a sub-volume of the three-dimensional image by the user using the input device of the treatment planning system.

16. The method of claim 15, wherein filtering is performed before defining the sub-volume.

17. The method of claim 15, wherein filtering is performed after defining the sub-volume.

18. The method of claim 15, wherein the sub-volume is a three-dimensional shape.

19. The method of claim 15, wherein filtering comprises isolating at least one of a target region and a critical structure within the three-dimensional image.

20. The method of claim 19, wherein isolating comprises turning one or more filter layers on or off within the three-dimensional image.

21. An apparatus, comprising:
a data storage device to store a three-dimensional image inclusive of a volume of interest structure; and
a user input device to receive user input from a user interacting directly within the 3D image, the user input identifying one or more locations within the three-dimensional image; and
a digital processing device coupled to the data storage device, the digital processing device to delineate the volume of interest structure of the three-dimensional image based on, at least in part, the received user input.

22. The apparatus of claim 21, wherein the digital processing device is further configured to create a set of voxels corresponding to the volume of interest structure.

23. The apparatus of claim 22, wherein the digital processing device is further configured to identify a contour of the volume of interest structure based on the set of voxels.

24. The apparatus of claim 22, wherein the data storage device is further configured to store the set of voxels corresponding to the volume of interest structure.

25. The apparatus of claim 21, further comprising a filter tool to distinguish the volume of interest structure from another structure in the three-dimensional image.

26. The apparatus of claim 21, further comprising a graphical display to display a volume rendering of the volume of interest structure.

27. The apparatus of claim 26, further comprising a sub-volume tool to allow a user to define a sub-volume of the three-dimensional image, wherein the sub-volume includes the volume of interest structure.

28. The apparatus of claim 27, wherein the graphical display is further configured to display the sub-volume and to not display other portions of the three-dimensional image excluded from the sub-volume.

29. A system comprising the apparatus of claim 21, the system further comprising:
a diagnostic imaging system coupled to the digital processing device, the diagnostic imaging system to obtain the three-dimensional image; and
a treatment delivery system coupled to the digital processing device, the treatment delivery system to deliver radiation treatment to the volume of interest structure.

30. The apparatus of claim 21, further comprising:
a graphical display to display the three-dimensional image; and
a user input device operatively coupled with the digital processing device to enable a user to delineating of the volume of interest structure within the three-dimensional image.

31. A non-transitory machine readable storage medium having instructions thereon, which instructions, when executed by a digital processing device, cause the digital processing device to perform the following, comprising:
display a three-dimensional image, wherein the three-dimensional image includes a volume of interest structure; and
receive input from a user input device, interacting directly within the 3D image, identifying one or more locations within the three-dimensional image; and
delineate the volume of interest structure within the three-dimensional image based on, at least in part, the received input.

32. The non-transitory machine readable storage medium of claim 31, having further instructions thereon, which further instructions, when executed by the digital processing device, cause the digital processing device to perform the following, comprising identify a set of voxels from the three-dimensional image to provide a binary description of the volume of interest structure.

33. The non-transitory machine readable storage medium of claim 31, having further instructions thereon, which further instructions, when executed by the digital processing device, cause the digital processing device to perform the following, comprising identify a contour of the volume of interest structure based on the set of voxels.

34. The non-transitory machine readable storage medium of claim 33, having further instructions thereon, which further instructions, when executed by the digital processing device, cause the digital processing device to perform the following, comprising identify a contour set of the volume of interest structure based on the set of voxels.

35. The non-transitory machine readable storage medium of claim 34, having further instructions thereon, which further instructions, when executed by the digital processing device, cause the digital processing device to perform the following, comprising identify a multi-contour set of the volume of interest structure based on the set of voxels.

36. The machine readable storage medium of claim 34, having further instructions thereon, which further instructions, when executed by the digital processing device, further cause the digital processing device to filter three-dimensional image.

37. The machine readable storage medium of claim 36, wherein filter of the three-dimensional image comprises turning one or more filter layers on or off within the three-dimensional image.

38. The machine readable storage medium of claim 34, having further instructions thereon, which further instructions, when executed by the digital processing device, further cause the digital processing device to define a sub-volume of the three-dimensional image.

39. The machine readable storage medium of claim 38, wherein the sub-volume is a three-dimensional shape.

40. The non-transitory machine readable storage medium of claim 31, having further instructions thereon, which further instructions, when executed by the digital processing device, cause the digital processing device to perform the following, comprising apply a filter to the three-dimensional image to distinguish the volume of interest structure from another structure.

41. The non-transitory machine readable storage medium of claim 31, having further instructions thereon, which further instructions, when executed by the digital processing device, cause the digital processing device to perform the following, comprising define a sub-volume of the three-dimensional image, wherein the sub-volume is inclusive of the volume of interest structure.

* * * * *